United States Patent [19]

Takeda et al.

[11] Patent Number: 4,876,458

[45] Date of Patent: Oct. 24, 1989

[54] APPARATUS FOR MEASURING PARTICLES IN LIQUID

[75] Inventors: Kazuo Takeda, Kokubunji; Yoshitoshi Ito, Ome; Noriaki Honma; Chusuke Munakata, both of Nishitama, all of Japan

[73] Assignee: Hitachi, Ltd., Tokyo, Japan

[21] Appl. No.: 250,615

[22] Filed: Sep. 29, 1988

[30] Foreign Application Priority Data

Oct. 2, 1987 [JP] Japan .................................. 62-247927
Jul. 18, 1988 [JP] Japan .................................. 63-177158

[51] Int. Cl.⁴ ............................................ G01N 15/06
[52] U.S. Cl. ...................................... 250/574; 356/339
[58] Field of Search .................... 250/573, 574, 575; 356/336, 338, 339, 340, 341, 342, 343

[56] References Cited

U.S. PATENT DOCUMENTS 4,113,386 9/1978 Lepper .................................. 250/574
4,375,334 3/1983 Gerber .................................. 358/336

Primary Examiner—David C. Nelms
Attorney, Agent, or Firm—Antonelli, Terry & Wands

[57] ABSTRACT

An apparatus for measuring particles in a liquid, with the apparatus including an arrangement for allowing a sample liquid to flow out from a nozzle into a gas in a stream, an arrangement for radiating light into the sample liquid stream coaxially with the axis of the stream, and an arrangement for collecting ways of light scattered by particles contained in the sample liquid stream at a point outside and by a side of the sample liquid stream and then detecting the collective light rays.

7 Claims, 4 Drawing Sheets

APPARATUS FOR MEASURING PARTICLES IN LIQUID

BACKGROUND OF THE INVENTION

This invention relates to a particle measurement system for determining the characteristics of particles in liquid from the rays of light scattered by the particles, and, more particularly, to an apparatus for measuring particles in liquid that eliminates stray light, which will produce noise during detection, and measures the particles so that the number of particles in the liquid is counted without omission.

The apparatus may be used to monitor dust in liquids which are used in the semiconductor manufacturing process or determine the size and kind of bacteria and biological cells in bioindustry.

Many improvements have been made to enhance the SN ratio during detection in a device in which the sample suspension flows through a transparent tube (flow cell) and light is irradiated against the sample suspension to determine the characteristics of particles contained in the suspension such as size and refractive index by detecting the scattering light from the particles, with most of the improvements relating to efforts to reduce the stray light that will produce noise, or eliminate the effect of the noise.

Unlike the measurement of particles in gases, the measurement of minute particles in liquids has the following problems. More particularly, since there are differences in the refractive index among the sample liquid, the material forming the flow cell through which the sample liquid is passed, and the open air, the scattering light and the reflected light from the boundaries between the three materials will form strong stray light.

To eliminate the strong stray light several conventional methods have been proposed as in, for example, Japanese Patent Laid-Open No. 114260/1979. A first proposed method consists in making the measuring region in the sample suspension very small, keeping the sensitive region as far away as possible from the boundary between the sample suspension and the wall of the flow cell to protect against the effect of stray light from the boundary. However, a disadvantage of this proposed method resides in the fact that since the measuring region is very small, the amount of sample liquid that can be measured per unit time duration is very small and that particles in regions other than the measuring region may not be counted by mistake. A second proposed method forms a flow of liquid around the sample suspension stream that has a refractive index equal to that of the sample suspension to eliminate stray light from the boundary between the sample suspension and the wall of flow cell, a method that uses a so-called sheath flow cell. With this method, since the stream of the sample suspension can be made narrower than the diameter of the irradiated light beam, a failure to count can be prevented. However, disadvantages of this proposed method resides in the fact that the sheath liquid flowing around the sample suspension stream must be a clean liquid containing no particles, and, to prevent the sample suspension stream from dispersing, it is necessary to produce a flow of sheath liquid which moves at higher speed and in larger quantity than the sample suspension. This means that the flow of the sheath liquid determines the upper limit of the sample suspension flow, so that in practice the flow of the sample suspension per unit duration of time is very small.

An apparatus to measure the characteristics of particles in a gas by detecting scattering light is also proposed in Japanese Patent Laid-Open No. 69683/1976 which employs a method of pouring the sample gas containing particles from a nozzle and irradiating light coaxially with the axis of the sample gas flow. Since the refractive index of the sample gas and that of the surrounding gas are almost equal, the irradiated light cannot be contained in the sample gas. To prevent any ommision in particle counting, a light beam larger in diameter than the sample gas stream must be applied and this means that there is an excess quantity of the irradiated light that is not effectively used. Also since the sample gas is poured out into another gas, the surrounding gas needs to be moved in the same steady flow as the sample gas to prevent sample gas flow dispersion.

Unlike the particle measurement of gas, measurement of particles in liquid must detect particles contained in a liquid which has a different refractive index than that of air. Therefore, the reflected light, diffracted light and scattering light from the surface of the flow cell through which the sample liquid is passed combine to form strong array light. To avoid the influence of the stray light, the common techniques that are available so far, as mentioned earlier, include focusing the incident light on a very small region of the sample liquid or pouring the sample liquid in a narrow stream by utilizing the sheath flow cell. These conventional techniques have the drawbacks that the entire cross section of the sample liquid stream is large as compared to the sensitive region, wasting a large proportion of sample suspension flow, and that when the sample suspension stream is made narrower than the diameter of the irradiated light beam to eliminate any omission in particle counting, the portion of the beam that is not applied to the sample suspension is wasted.

SUMMARY OF THE INVENTION

The object of this invention is to provide an apparatus for measuring particles in liquid that can overcome the above problems experienced with the conventional techniques, eliminate stray light and wasted irradiated light, and prevent any omission in particle counting.

In accordance with advantageous features of the present invention means are provided for allowing the sample liquid to flow out from a nozzle into an open air in a stream along with means for irradiating light into the stream of sample liquid coaxially with the axis of the stream. Additionally, means are provided for collecting and detecting, at a point outside and by the side of the sample liquid stream, the scattering light from minute particles in the sample liquid.

The invention utilizes the difference in the refractive index between the air and the sample liquid to contain the incident light in the sample liquid, thereby eliminating the stray light and the wasting of irradiated light and also preventing any omission in particle counting.

The refractive index of liquid is generally larger than that of gas. For instance, the refractive index of air is 1.00 as opposed to 1.33 for water. Therefore, if the liquid is made to flow in a stream and light is passed through the stream coaxially with its axis, the light is totally reflected inside the stream, so that the liquid stream has the function of an optical guide like an optical fiber. Since the irradiated light is contained in the stream of liquid, no stray light is produced. With the optical fiber, a cladding material which has a smaller refractive index than that of a core material must be clad over the core which works as a light wave guide. The invention, however, requires only the formation of the running stream of the sample liquid. With only this arrangement, the light can be irradiated over the entire cross-sectional area of the sample liquid stream, thus making it possible for all the particles in the sample liquid to be counted without omission.

DESCRIPTION OF THE PREFERRED EMBODIMENTS

Figure 1:
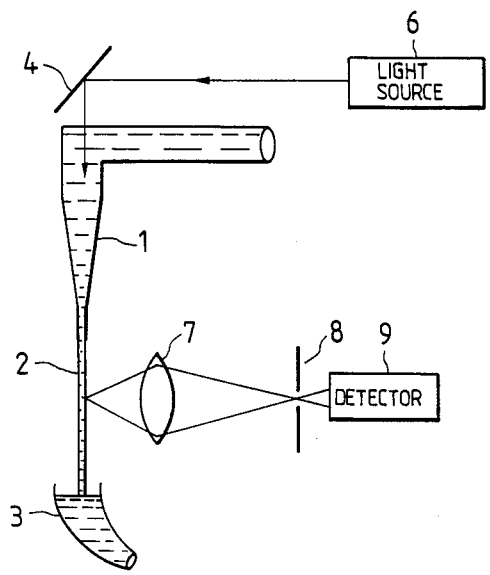
FIG. 1 is a basic construction of a first embodiment of the invention.

As shown in the the first embodiment of FIG. 1, a sample suspension 2 is poured out into an open air from a black nozzle 1. In the embodiment the nozzle 1 has the inner diameter of 0.4 mm and thus the outer diameter of the sample suspension 2 running in a stream is 0.4 mm. The pouring from the nozzle of the sample suspension 2 is carried out in a free-fall method with the nozzle connected to a suspension liquid tank (not shown) located at a height. This may be replaced with a method in which a pump (not shown) is used to pump the sample suspension under a constant pressure. In the embodiment of FIG. 1 the sample suspension 2 is water containing dust. The light from a light source 6 is irradiated in the same direction of the flow of the streamed sample suspension 2 by using a mirror 4. The applied light is a general visible light beam condensed to a diameter of almost 1 mm. It is possible to use a laser beam instead of a visible light beam.

Since there is a difference in the refractive index between the sample suspension and the air (the sample suspension has a greater refractive index), the radiated beam is contained in the stream of sample liquid by a total reflection in the liquid. The light beam also is radiated over the entire cross-sectional area of the sample liquid stream. The rays scattered by the particles in the sample liquid are directed in many directions and also in the direction perpendicular to the surface of the sample liquid stream and thus are not contained in the sample liquid. The scattered rays are collected by a lens 7 and detected by a detector 9 with the sensitive region restricted by an aperture 8. The transmitted light and the sample liquid enter a black tube 3 for recovery.

In the arrangement of FIG. 1, the scattering rays from particles can be detected with no stray light present. The light is applied over the entire cross-sectional area of the sample liquid stream, so that all the particles in the liquid can be measured without omission.

Figure 2:
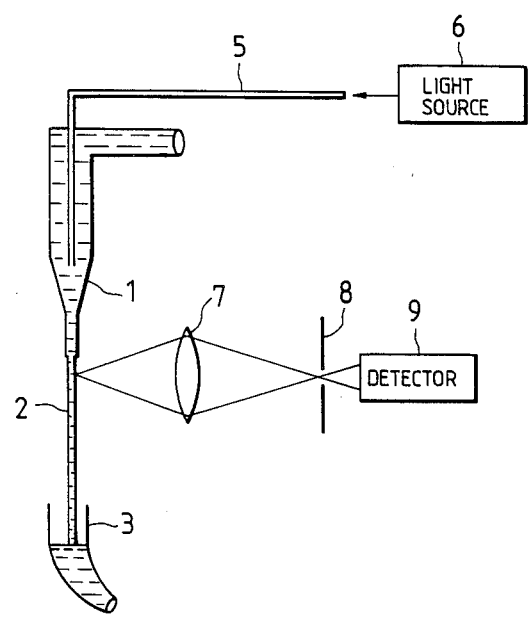
FIG. 2 is a basic construction of a second embodiment of the invention.

In the second embodiment of FIG. 2, to introduce a light beam into the sample suspension 2, an optical fiber 5 is used.

Figure 3:
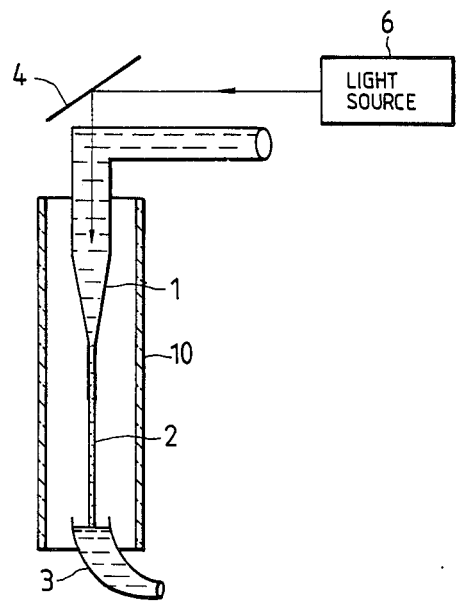
FIGS. 3 and 4 are basic constructions of third and fourth embodiments which are the first and second embodiments attached with additional components.
Figure 4:
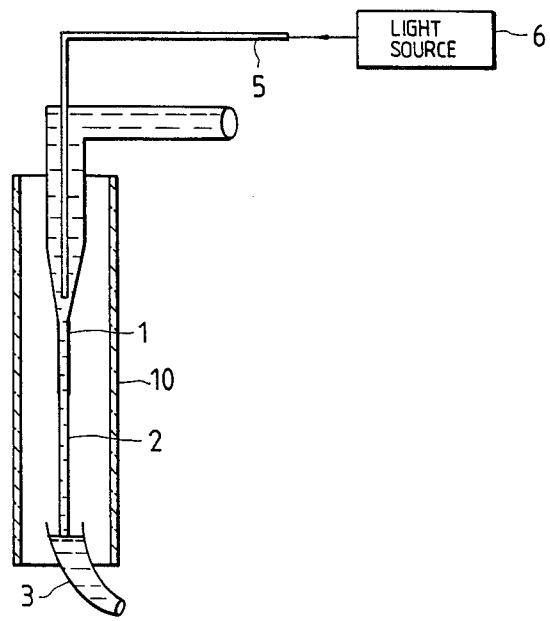

In the third and fourth embodiments of FIGS. 3 and 4 the running stream of the sample suspension 2, the lower end of the nozzle 1 and the upper end of the black tube 3 in the first and second embodiments of FIGS. 1 and 2 are enclosed by a glass tube 10. With this arrangement, the dust in the air can be prevented from getting into the sample liquid, thereby improving the accuracy of measurement.

The following explanation relates to the construction for suppressing the generation of stray light by referring to the second embodiment of FIG. 2 and the fourth embodiment of FIG. 4.

First, the principle of this embodiment is described.

Figure 5:
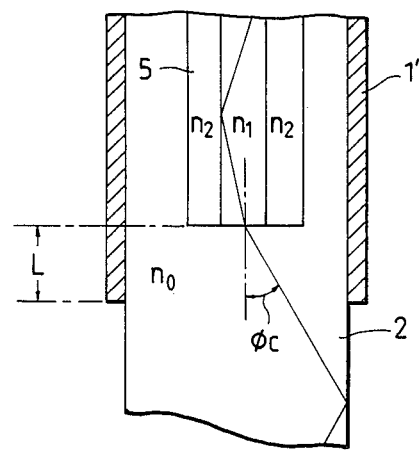
FIG. 5 is a cross-sectional view of still another embodiment showing the principle of the invention.

FIG. 5 is an explanatory view regarding the angle of light beam emitted from the end of the optical fiber into the sample liquid of water. The optical fiber 5 includes a core (refractive index n1) and a cladding (refractive index n2). The critical angle $\Phi c$ of light emitted from the optical fiber 5 is given by the following relationship:

$$\phi c = \sin^{-1}(\sqrt{(n1^2 - n2^2)}/n0)$$

where: n0 (=1.33) is the refractive index of the sample water 2. Using general values n1=1.5 and n2=1.44, the critical angle $\Phi c$ is calculated to be 24°. The maximum angle for total reflection of light in the sample water 2 surrounded by air (refractive index=1.0) is 41.2°, which is larger than the critical angle $\Phi c$. Therefore, the light beams going out from the optical fiber 5 are totally reflected and contained in the stream of sample water 2 enclosed by air. These light beams are radiated over the entire cross section of the stream of the sample water 2. The particle measurement apparatus for liquid according to this invention therefore has no wasted light that is not used for measurement, and is able to count the particles without omission. With the embodiment of FIGS. 2 and 4, however, there remains a problem that in the region where the stream of sample water 2 is enclosed by the nozzle end 1' the light beams are not totally contained producing stray light.

The above problem is eliminated by positioning the front end of the optical fiber so that the light beams emitted from the optical fiber end will not strike the inner wall of the nozzle.

Figure 6:
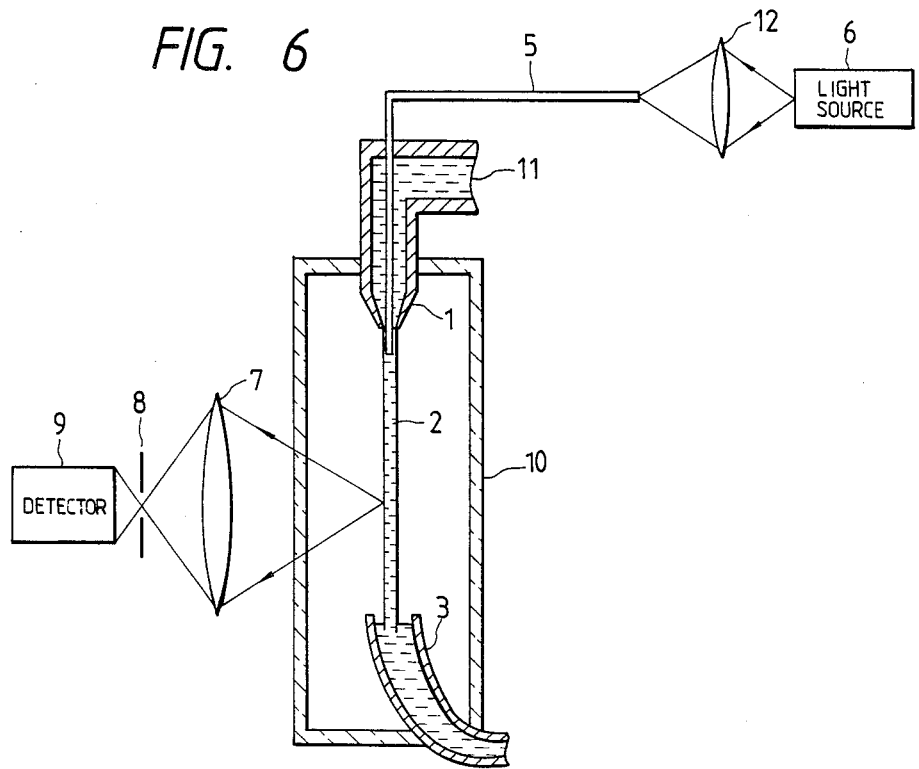
FIGS. 6 and 7 are basic constructions of fifth and sixth embodiments utilizing the principle of FIG. 5.

In the fifth embodiment of FIG. 6, the front end of the optical fiber 5 projects out of the nozzle end and the sample liquid used is water containing dust. The sample water 2 is supplied through the sample water supply pipe 11 and allowed to flow out from the nozzle 1 into an open air in a stream. In this embodiment, with the inner diameter of the nozzle 1 is being 0.4 mm and thus the outer diameter of the stream of the sample water being about 0.4 mm. The base end of the sample water supply pipe 11 opposite to the nozzle 1 is connected to a sample liquid tank (not shown) located at a height and the sample water 2 is allowed to fall freely by gravity from the nozzle 1. The water may be supplied under a constant pressure by a pump (not shown). The light beams from the light source 6 are focused by a lens 12 to enter the optical fiber 5 which has a core diameter of 0.05 mm and a cladding outer diameter of 0.1 mm. General visible light is used as the light to be radiated. A laser beam may also be used instead.

The optical fiber 5 is introduced through the sample water supply pipe 11 and arranged so that the front end of the optical fiber 5 projects from the end of the nozzle 1. Thus, the light beams emitted from the optical fiber 5 are, as explained referring to FIG. 5, totally reflected and contained in the stream of sample water 2 because there is a difference in the refractive index between the sample water 2 and the air (the sample water has a greater refractive index). Moreover, these beams are radiated over the entire cross section of the sample water 2 stream.

The particles in the sample water scatter the incident light in many directions and also in a direction perpendicular to the surface of the sample water 2 and, therefore, the scattering rays of light are not contained in the water stream. The scattering rays are collected by a lens 7 onto a detector 9 with the sensitive region restricted by a slit 8. The transmitted beams and the sample water 2 enter the black tube 3 for recovery. To eliminate the effect of dust in the air, the nozzle 1 and the black tube 3 are enclosed by a transparent dust protection tube 10.

The embodiment of FIG. 6 permits detection of the rays of light scattered by particles with no stray light present. Since the entire cross section of the sample water stream is radiated with light, all the particles contained in the sample water 2 can be counted without any omission in counting.

Figure 7:
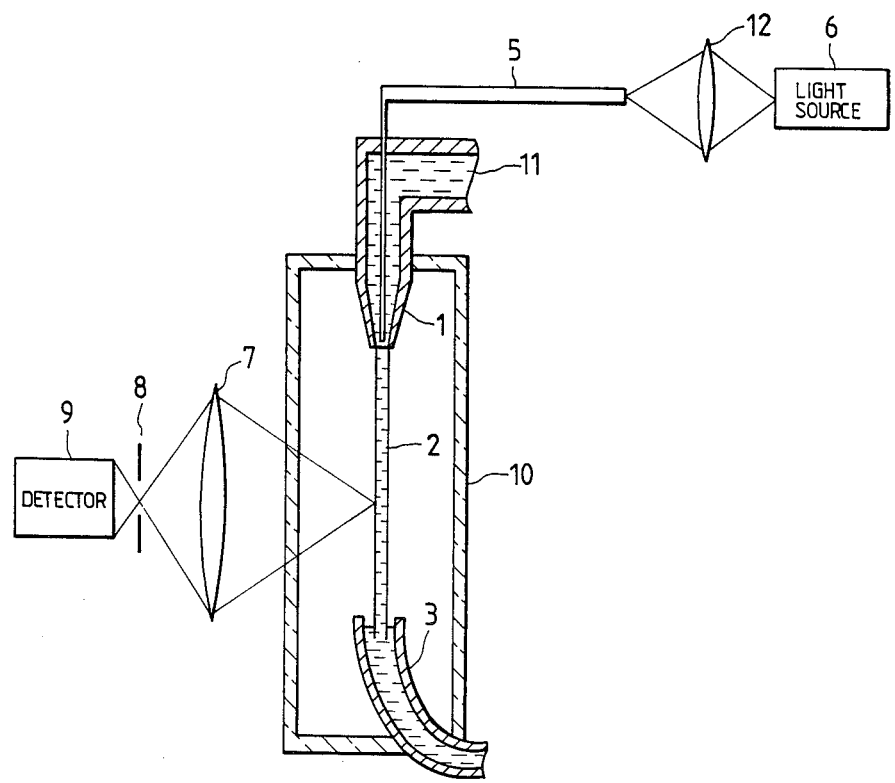

In the sixth embodiment of FIG. 7, the front end of the optical fiber 5 is retracted inside the nozzle 1 to such an extent that the light emitted from the optical fiber will not strike the inner wall of the nozzle 1. The sample liquid used is water containing dust, as with the above-described embodiments. The point in which the embodiment of FIG. 7 differs from the embodiment of FIG. 6 is that the end of the optical fiber 5 is located inside the end of the nozzle 1. Other parts are identical with those of FIG. 6.

As shown in FIG. 7 and FIG. 5, the front end of the optical fiber 5 is located inside the end of the nozzle 1 by a distance L. The allowable limit Lc of the distance L is determined from the critical angle $\Phi c$ of a beam emitted from the optical fiber 5, the diameter D of the stream of sample water 2 and the core diametered of the optical fiber 5. That is, $Lc \cdot \tan \Phi c = D/2 - d/2$. From this we obtain $Lc = (D/2 - d/2)/\tan \Phi c$. With the distance L set smaller than the allowable limit Lc, the light emitted from the optical fiber 5 can be prevented from striking the inner wall of the nozzle 1, thus eliminating the stray light.

In addition to the advantages of the embodiment of FIG. 6, the embodiment of FIG. 7 has the advantage that the location of the optical fiber end inside the nozzle end improves the flow stability of the sample water stream and the steadiness of flow speed.

As mentioned above, the present invention can provide a particle measurement apparatus for liquid which eliminates stray light and counts all the particles in the sample liquid with not a single particle left out.

What is claimed is:

1. An apparatus for measuring particles in a liquid the apparatus comprising:
   a sample liquid supply means for allowing the sample liquid to flow out from a nozzle into a gas in a stream;
   a light radiation means for radiating light into an sample liquid stream coaxially with the axis of the stream; and
   a scattering light detection means for collecting rays of light scattered by particles contained in a sample liquid stream at a point outside and by the side of the sample liquid stream and then detecting the collected light rays.

2. An apparatus for measuring particles in liquid as set forth in claim 1, wherein the sample liquid supply means includes a sample liquid supply tube, a nozzle provided at one end of the sample liquid supply pipe, and a sample liquid recovery tube located opposite to the nozzle with a gap therebetween.

3. An apparatus for measuring particles in liquid as set forth in claim 2, wherein the sample liquid recovery tube traps the radiated light.

4. An apparatus for measuring particles in liquid as set forth in claim 1, wherein the light radiation means includes a light source and an optical fiber means for conducting light from the light source.

5. The apparatus for measuring particles in liquid as set forth in claim 1, wherein the light radiation means includes a optical fiber means, and a front end of the optical fiber means is located so that light emitted from the optical fiber means will not strike and inner wall of the nozzle.

6. An apparatus for measuring particles in liquid as set forth in claim 5, wherein the front end of the optical fiber means projects out of the end of the nozzle.

7. An apparatus for measuring particles in liquid as set forth in claim 2, wherein a transparent tube encloses and outer circumference of the sample liquid stream, extending from a lower end of the nozzle to and upper end of the sample liquid recovery tube.

* * * * *